United States Patent
Haase et al.

(10) Patent No.: US 12,115,014 B2
(45) Date of Patent: Oct. 15, 2024

(54) MOST RELEVANT X-RAY IMAGE SELECTION FOR HEMODYNAMIC SIMULATION

(71) Applicant: KONINKLIJKE PHILIPS N.V., Eindhoven (NL)

(72) Inventors: Christian Haase, Hamburg (DE); Cornelis Willem-Johannes Immanuel Spoel, Helmond (NL); Martijn Anne Van Lavieren, Utrecht (NL); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 445 days.

(21) Appl. No.: 17/294,740

(22) PCT Filed: Nov. 27, 2019

(86) PCT No.: PCT/EP2019/082804
§ 371 (c)(1),
(2) Date: May 18, 2021

(87) PCT Pub. No.: WO2020/109422
PCT Pub. Date: Jun. 4, 2020

(65) Prior Publication Data
US 2022/0015730 A1    Jan. 20, 2022

(30) Foreign Application Priority Data
Nov. 28, 2018  (EP) ...................................... 18208852

(51) Int. Cl.
*A61B 6/00*    (2024.01)
*A61B 6/50*    (2024.01)
*G06T 7/00*    (2017.01)

(52) U.S. Cl.
CPC ............ *A61B 6/5217* (2013.01); *A61B 6/481* (2013.01); *A61B 6/504* (2013.01); *G06T 7/0016* (2013.01);
(Continued)

(58) Field of Classification Search
CPC ....... A61B 6/5217; A61B 6/481; A61B 6/504; A61B 6/507; G06T 7/0016;
(Continued)

(56) References Cited

U.S. PATENT DOCUMENTS 5,848,198 A * 12/1998 Penn ...................... G06T 7/0012
                                                    382/276
6,343,142 B1 * 1/2002 Tsutamori ............... G06T 7/001
                                                    382/128
(Continued)

FOREIGN PATENT DOCUMENTS

WO    2018002195 A1    1/2018

OTHER PUBLICATIONS

International Search Report and Written Opinion of PCT/EP2019/082804, dated Feb. 14, 2020.
(Continued)

*Primary Examiner* — Santiago Garcia

(57) ABSTRACT

A method and apparatus for selecting one or more diagnostic images to generate a physiological model are provided in which a set of candidate images is determined for review by a user, in particular by a physician. The candidate images are hereby determined using one or more target measures, such as a density measure, a motion measure, a deviation measure or the like, that have been derived for each diagnostic image of an X-ray angiography series and by analyzing said target measure. Subsequently, a suitability score that is based on
(Continued)

the requirements of the physiological model that shall be generated from the selected candidate images is assigned to each candidate image.

20 Claims, 3 Drawing Sheets

(52) U.S. Cl.
CPC ............... *G06T 2207/10116* (2013.01); *G06T 2207/30101* (2013.01)

(58) Field of Classification Search
CPC . G06T 2207/10116; G06T 2207/30101; G06T 2207/30168; G06T 7/0002
See application file for complete search history.

(56) References Cited

U.S. PATENT DOCUMENTS

| | | | |
|---|---|---|---|
| 8,605,976 B2 | 12/2013 | Diamant | |
| 9,014,453 B2 | 4/2015 | Steinberg | |
| 10,108,780 B2* | 10/2018 | Burton | G16H 10/60 |
| 10,176,408 B2* | 1/2019 | Paik | G06F 18/29 |
| 2003/0091641 A1* | 5/2003 | Tiller | A01N 43/40 424/78.22 |
| 2005/0043227 A1* | 2/2005 | Compernolle | G01N 33/74 435/7.1 |
| 2006/0046279 A1* | 3/2006 | Truong | G01N 33/569 435/29 |
| 2009/0257554 A1* | 10/2009 | Parks | A61B 6/12 378/62 |
| 2009/0324029 A1* | 12/2009 | Araikum | G06T 5/003 382/128 |
| 2010/0161023 A1* | 6/2010 | Cohen | G06T 7/13 623/2.11 |
| 2012/0201442 A1* | 8/2012 | Beck | G06T 7/12 382/131 |
| 2014/0039928 A1* | 2/2014 | Burton | G06F 21/32 705/3 |
| 2015/0161790 A1* | 6/2015 | Takahashi | A61B 6/12 600/425 |
| 2015/0228115 A1* | 8/2015 | Wakai | A61B 6/466 345/420 |
| 2015/0262358 A1 | 9/2015 | Schormans | |
| 2016/0012613 A1* | 1/2016 | Okerlund | G06T 11/003 382/131 |
| 2016/0171682 A1 | 6/2016 | Abedini | |
| 2018/0071452 A1 | 3/2018 | Sharma | |
| 2018/0263574 A1* | 9/2018 | Zannoli | G09G 5/006 |
| 2018/0312999 A1* | 11/2018 | Shah | G16C 20/60 |
| 2018/0369611 A1* | 12/2018 | Owens | A61N 5/1071 |
| 2019/0220606 A1* | 7/2019 | Li | G06F 21/6245 |
| 2019/0287247 A1* | 9/2019 | Duchesne | G06T 7/0016 |
| 2020/0098468 A1* | 3/2020 | Gotman | G16H 30/20 |
| 2020/0110923 A1* | 4/2020 | Tanikawa | G06V 20/693 |
| 2021/0298662 A1* | 9/2021 | Gharagouzloo | G16H 30/20 |

OTHER PUBLICATIONS

Dehkordi, Maryam Taghizadeh "Extraction of the Best Frames in Coronary Angiograms for Diagnosis and Analysis", Journal of Medical Signals and Sensors, 2016.

Syeda-Mahmood, T. et al "Automatic Selection of Keyframes from Angiogram Videos", 2010 International Conference on Pattern Recognition.

* cited by examiner

MOST RELEVANT X-RAY IMAGE SELECTION FOR HEMODYNAMIC SIMULATION

CROSS-REFERENCE TO PRIOR APPLICATIONS

This application is the U.S. National Phase application under 35 U.S.C. § 371 of International Application No. PCT/EP2019/082804, filed on Nov. 27, 2019, which claims the benefit of European Patent Application No. 18208852.6, filed on Nov. 28, 2018. These applications are hereby incorporated by reference herein.

FIELD OF THE INVENTION

The present invention relates to a method for image selection, a corresponding apparatus and a computer program. In particular, the present invention relates to a method which employs the use of a suitability score to automatically select one or more images from a set of candidate images whereby the suitability score is dependent on the subsequent usage of the selected images, in particular on the kind of fluid dynamics simulation to be performed on the basis of said selected images.

BACKGROUND OF THE INVENTION

Diagnostic images acquired using X-ray angiography provide an important tool for obtaining information about the coronary arteries. These images allow to accurately evaluate a coronary disease by means of a variety of different approaches.

One such approach is the image-based "virtual" determination of hemodynamic measures, such as the Fractional Flow Reserve (FFR) or Instantaneous Wave-Free Ratio (iFR). Both, FFR as well as iFR, are a measure for the pressure drop of the blood along a vessel of interest, e.g. due to a stenosis in said vessel of interest. They may be determined as the ratio of the pressure distal the stenosis ($P_d$) to the pressure in the aorta ($P_a$).

In the past, FFR and/or iFR measurements were typically performed invasively, by measuring the pressure at a position distal from and a position proximate to the lesion using a respective intravascular measurement device including a pressure sensor. For FFR, these invasive measurements have to be performed during maximal blood flow, i.e. under hyperemia, which may cause discomfort in the patient. In contrast, iFR measurements may be performed at rest during a specific period in diastole, thereby avoiding the necessity to induce hyperemia in the patient.

In recent years, efforts have been taken to determine the FFR and/or iFR values non-invasively by means of the above-mentioned virtual approach. In accordance with the virtual approach, the fluid dynamics in the coronary arteries of a patient are simulated on the basis of a physiological model including a fluid dynamics model representing the blood flow through the vessel or vessels of interest.

SUMMARY OF THE INVENTION

It is an object of the present invention to provide a method of image selection that allows to select the image or images most suitable for such physiological modelling with minimum user interaction in a reduced amount of time.

More specifically, it is an object of the invention to provide a method and an apparatus that allows to automatically pre-select a set of candidate images from one or more series of diagnostic images to present to a user, in particular a physician, such that the user has to review a reduced amount of images. Even more particularly, it is an object of the invention to provide a method and an apparatus which allows a user to quickly determine the suitability of a set of candidate images for a fluid dynamics simulation of a particular kind.

This objective is achieved by a method of selecting one or more diagnostic images for generating a physiological model, the method being a computer-implemented method comprising the steps of obtaining a plurality of diagnostic images of a target structure, deriving a plurality of target measures comprising at least one respective target measure for each of the plurality of diagnostic images, analyzing the plurality of target measures to select a set of candidate images, and assigning a suitability score to each candidate image in the set of candidate images, the suitability score indicating a suitability of the respective candidate image for generating the physiological model.

In particular, one or more of these steps may be implemented as a unit of a corresponding apparatus. In an example, the obtaining step may be implemented by means of an input unit, the deriving step may be implemented by means of a computation unit, the analyzing step may be implemented by means of an analyzation unit and the selecting step and the step of assigning a suitability score may be implemented by means of a selection unit.

The physiological model may be generated on the basis of a plurality of diagnostic images of the coronary vasculature that have been acquired during X-ray angiography. Preferably, not all diagnostic images that have been acquired are used, but rather a selection thereof. In particular, the selection is performed such that the most suitable diagnostic images are used to generate the physiological model. Which and how many diagnostic images are most suitable for a particular physiological model hereby largely depends on the desired results of the fluid dynamics simulation.

The plurality of diagnostic images may particularly refer to a series of diagnostic images having been acquired by means of a medical imaging modality. In some embodiments, the plurality of diagnostic images may refer to multiple series of diagnostic images acquired for one patient, such that the selection process is performed amongst multiple series. This allows to combine the information provided in different series of diagnostic images and may result in improved accuracy. The one or more series of diagnostic images may be acquired using any medical imaging modality as long as it allows to visualize and identify the target structure. As an example for suitable medical imaging modalities computed tomography, magnetic resonance imaging, ultrasound imaging or the like are mentioned.

In some embodiments, the one or more series of diagnostic images may particularly refer to one or more series comprising a plurality of X-ray angiography images, in particular two-dimensional X-ray angiography images. For X-ray angiography, a contrast agent may be introduced into the target structure. X-ray angiography imaging may then be performed on the target structure during contrast agent inflow and contrast agent outflow. That is, the series of X-ray angiography images may comprise a subset of diagnostic images representing the contrast agent inflow, a subset of diagnostic images representing the contrast agent filled target structure and a subset of diagnostic images representing the contrast agent outflow. In this case, it may be beneficial to select diagnostic images as candidate images that have a low degree of foreshortening and low overlap. Further, in any case, the contrast agent filling should be sufficient to provide suitable contrast.

A selected one or more diagnostic images may be used for generating a physiological model. In that context, the term physiological model may particularly refer to a model of the target structure including a geometric model representing the target structure's geometry and/or a fluid dynamics model representing the fluid dynamics through said target structure.

A target structure may particularly refer to a vessel of interest or a plurality of vessels of interest that shall be evaluated for a particular patient. In some embodiments, the target structure may particularly refer to the coronary vasculature of a patient, said coronary vasculature including one or more vessels of interest.

In such a case, the physiological model may be generated from the one or more selected diagnostic images by segmenting the vessel of interest or vessels of interest represented in the selected diagnostic images and generating the geometric model representing the vessel geometry of the vessel of interest and/or the fluid dynamics model representing the fluid dynamics through the vessel of interest. In some embodiments, the geometric model may particularly correspond to a two-dimensional or quasi-three dimensional geometric model in which the third dimension is approximated.

In some embodiments, the fluid dynamics model may particularly correspond to a lumped parameter fluid dynamics model. In such a lumped parameter fluid dynamics model, the fluid dynamics of the vessels are approximated by a topology of discrete entities. As an example, a vessel tree may be represented by a topology of resistor elements each having a particular resistance. Accordingly, the outlet at a distal end of the vessel is also represented by a particular resistor element. This resistor element is then connected to ground such as to represent the connection of the vessel to the venous system. Similarly, respective resistor elements may be connected to the series of resistor elements representing the vessel of interest, such as to represent the outflow from the vessel of interest at certain bifurcations. These resistor elements may typically also be connected to ground. Lumped parameter fluid dynamics models reduce the number of dimensions compared to other approaches such as Navier-Stokes or the like. Accordingly, using a lumped parameter fluid dynamics model may allow for a simplified calculation of the fluid dynamics inside the vessels and are thus particularly beneficial in terms of processing time.

The term target measure may particularly refer to one or more properties of the target structure as represented in the at least one diagnostic image. In this context, the term target measure may particularly refer to a target structure density measure, i.e. a quantitative measure indicative of how much of the target structure is visible in the respective diagnostic image, a motion measure indicative of a motion of the target structure, e.g. between two consecutive diagnostic images, an overlap measure indicating the amount of overlap in a diagnostic image of the target structure, a visibility measure indicating the visibility, e.g. of the edges, of the target structure and/or a deviation feature indicating the deviation of a desired target acquisition time of a particular diagnostic image. Each of these target measures may influence the suitability of a particular diagnostic image for generating the physiological model. As indicated, one or more such target measures may be derived for each one of the diagnostic images. Subsequently, the target measure may be analyzed to select, from the plurality of diagnostic images, a set of appropriate candidates that may be used to generate the physiological model. Hereby, it shall be understood that the influence that each of the target measures has on the suitability may vary depending on the kind of physiological model to be generated.

As an example, in some embodiments, the physiological model is used to extract geometric parameters of the target structure, such as the vessel dimensions in a vasculature. In such a case a single diagnostic image may suffice for modeling. Hereby, in order to have the geometric modeling be particularly accurate, factors such as segmentation accuracy and motion of the target structure, for example in case of a coronary target structure due to the cardiac phase, are important requirements. That is, the method will perform suitability scoring that takes into account factors such as overlap in the target structure, contrast agent filling, sharpness of the target structure's individual features, visibility of relevant bifurcations, as well as the motion phase, such as the cardiac phase.

Based on this suitability scoring, the method may output one or more candidate images that are considered particularly suitable for geometric modeling. In some embodiments, the output may be provided to a user and the user may then review these outputs and decide which candidate image to be used for the modeling. In some embodiments, the output may be provided directly to a processor capable of performing the modeling. The processor may then use any of the suitable candidates at random or may select one of the candidate based on the suitability score.

In some embodiments, the physiological model including the fluid dynamics model is used for more complex hemodynamic simulations. In these cases, multiple diagnostic images may be necessary to generate the physiological model. In some embodiments, at least one diagnostic image representing the contrast agent inflow into the target structure, at least one diagnostic image representing the contrast agent outflow from the target structure and at least one diagnostic image representing the fully contrast agent filled target structure may be needed. These three (or more) particular diagnostic images at these three different phases may particularly be used to determine a measure of the inflow and outflow speed of the contrast agent (from diagnostic images representing all three phases) and, in the case of a coronary vasculature as a target structure, a measure of the myocardial perfusion which may be used as a boundary condition for the hemodynamic simulation (from the diagnostic images representing the outflow phase). Further, a diagnostic image representing the full filling phase may particularly allow to review the details of the target structure most accurately. In the case of a vasculature, i.e., a vessel of interest to be modelled, this allows to identify and determine possible branches from the vessel of interest and, thus, to integrate respective outlets into the physiological model. This overall enhances the accuracy of the hemodynamic simulation. The above-mentioned requirements for suitable candidate images such as overlap, contrast agent filling, sharpness of the target structure's individual features as well as the motion phase are likewise to be accounted for.

Depending on the requirements of the physiological model and, thus, the complexity of the hemodynamic simulation, the candidate images are thus identified from the analysis of the target measure.

To that end, the term candidate image may refer to a diagnostic image that has been selected as a possible candidate for further physiological modeling. In some embodiments, typically a set of candidate images is identified, out of which the user or a processor may choose a desired candidate. In some embodiments, only a single candidate image may be identified.

Each identified candidate image is then assigned a respective suitability score. The term suitability score may hereby particularly refer to a quantitative value indicating the suitability of the respective candidate image for the physiological modeling of the target structure. It shall be understood that the suitability score may not be necessarily be visualized and may also refer to a score that is determined solely for the purpose of internal processing by the processor implementing the physiological modeling.

In some embodiments, the suitability score may particularly refer to a score assigned depending on the categorization of a candidate image representing the target structure during contrast agent inflow, contrast agent outflow or in the full filling phase and one or more respectively weighted target measures, such as the overlap measure identified for the target structure in that particular image, the motion measure determined for the target structure in said image, and the like. The weighting of each of these measures is adjusted in accordance with the influence of said feature for the physiological model, i.e. the weighting may be adjusted in accordance with the specific requirements of the respective physiological model.

Providing a suitability score based on the requirements of the respective physiological model may thus be used to implement a straightforward and less time-consuming image selection which allows a user to identify a suitable image from a large plurality of images without the need for much user interaction.

In some embodiments, the deriving of the plurality of target measures comprises generating, for each of the plurality of diagnostic images, a respective processed image, the generating comprising assigning a plurality of quantitative values to a plurality of pixels of the respective diagnostic image, the quantitative value indicating a probability that the pixel represents the target structure, and deriving a target structure density measure for each of the plurality of diagnostic images based on the plurality of quantitative values. In some embodiments, the target structure density measure for each of the plurality of images is derived based on a sum of the plurality of quantitative values.

In some embodiments, the deriving the target measure comprises a deriving of a target structure density measure. Hereby, the term target structure density measure may particularly refer to a quantitative measure indicative of how much of the target structure is visible in the respective diagnostic image. That is, diagnostic images representing target structures with a large degree of contrast agent filling will have a higher value for the target structure density measure and diagnostic images representing target structures with a low degree of contrast agent filling will have a lower value for the target structure density measure.

It shall be understood that, in case of a series of diagnostic images acquired from contrast agent inflow to contrast agent outflow, the diagnostic images representing the fully contrast agent filled target structure will have a target structure density measure of a higher value than the diagnostic images representing the target structure during the inflow and outflow phase. Hereby, it shall be understood that there may particularly be one target structure density measure per diagnostic image. In case the target structure corresponds to a coronary vasculature, the target structure density measure may particularly indicate the amount of the vessels visible in each particular diagnostic image.

The deriving the target structure density measure is achieved by processing each of the plurality of diagnostic images using an image processing algorithm specifically tuned for the target structure. The output of this processing step is a processed image, i.e. one processed image is generated for each diagnostic image.

In some embodiments, each pixel of the respective diagnostic image may be assigned a quantitative value between 0 and 1 indicating a chance or probability of said pixel belonging to the target structure to generate the processed image. That is, pixels in the diagnostic images having a high probability of belonging to the target structure will be assigned with a value close to 1 and pixels with a high probability of belonging to the background will be assigned with a value close to 0. The processed image thus corresponds to a pixel map of values between 0 and 1.

A target structure density measure may then be derived based on this pixel map by considering the quantitative values assigned to each of this pixel. In some embodiments, this may be achieved by determining the target structure density measure as a sum of all quantitative values within one processed image. Given that pixels representing the target structure have a higher value than pixels representing background and given that the target structure becomes more visible the more contrast agent filling is provided in the target structure, summing the quantitative values to obtain the target structure density measure will yield a target structure density measure with a higher value for the contrast filled target structure. Accordingly, a high value for the target structure density measure is directly proportionate to a diagnostic image in which the target structure is clearly visible. Further, given that less contrast agent will result in more background, the target structure density measure obtained as a sum from the quantitative values of the pixel map will be lower in the contrast agent inflow and contrast agent outflow phase, as well as in cases where the target structure is poorly visible for other reasons.

Given that the processed image is derived from the diagnostic image, the thus determined value for the target structure density measure may be directly correlated to the corresponding diagnostic image. As a result, the value obtained for the target structure density measure for each diagnostic image may be determined by first image processing the diagnostic image to obtain the processed image comprising the pixel map and subsequently summing up the quantitative values for each pixel to obtain the target measure.

According to some embodiments, the selecting the set of candidate images comprises analyzing the derived target structure density measure as a function of the measurement time, and obtaining, based on said analyzing, a first subset of candidate images representing a contrast agent inflow phase, a second subset of candidate images representing a contrast agent full filling phase, and a third subset of candidate images representing a contrast agent outflow phase.

In some embodiments, the selecting of the candidate images may comprise an analyzing of the target structure density measure as a function of measurement time. Hereby, the term measurement time may particularly refer to the time between the starting of the contrast agent inflow and the contrast agent outflow, during which a plurality of diagnostic images is acquired. The amount of data points for this analysis depends on the timing of the diagnostic imaging, i.e. there is one data point indicating the target structure density measure for each diagnostic image acquired.

The resulting curve of the target structure density measure over time allows to determine, for each one of the diagnostic images, whether said diagnostic image represents the contrast agent inflow phase, the full-filling phase or the contrast agent outflow phase. That is, upon selection of any of these images as candidates, the thus selected candidate images may be subdivided into three subsets corresponding to the three phases.

As indicated herein above, the amount of images that need to be selected for the generation of the physiological model may depend on the kind of physiological model that shall be generated, i.e. on the kind and amount of information to be derived from said physiological model.

In case of more complex physiological modeling, it may be necessary to select at least three—or more—diagnostic images. In some embodiments, each these at least three diagnostic images shall correspond to a different phase of the contrast agent flow, i.e. one diagnostic image has been obtained during contrast agent inflow, one image has been obtained as the target structure has been fully filled with contrast agent and one diagnostic image has been obtained during contrast agent outflow. That is, in some embodiments, the set of candidate objects, i.e. of diagnostic images selected as being suitable, may be subdivided into three subsets, whereby each subset corresponds to one of the above-mentioned contrast agent time phases, designated contrast agent inflow phase, full filling phase and contrast agent outflow phase, respectively.

Hereby, the contrast agent inflow phase corresponds to the time from injection of the contrast agent until the contrast agent has fully flowed into the target structure. The full filling phase corresponds to the time during which the contrast agent remains in the target structure. The contrast agent outflow phase corresponds to the time from the end of the contrast agent injection until the contrast agent has fully exited the target structure.

The identifying whether a particular diagnostic image—i.e. a potential candidate image—corresponds to a particular phase may particularly be performed by considering the curve representing the plurality of target structure density measures as a function of the measurement time which covers all three phases. Hereby, the images belonging to the contrast agent inflow phase typically have a low to intermediate target structure density measure which increases with increasing measurement time. The images belonging to the full filling phase correspond to the target structure density measures having the peak values of the curve. Finally, the images belonging to the contrast agent outflow phase correspond to the target structure density measures having a low to intermediate value which is decreasing with increasing measurement time.

It shall be understood that the curve representing the target structure density measure as a function of measurement time may be displayed to a user, but may also correspond to a "virtual" curve internally processed in the apparatus for analyzing purposes only.

In the above-cited embodiment, the at least three diagnostic images selected as candidates for generating the physiological model each correspond to a different filling phase of the contrast agent inflow into the target structure. It shall be understood, though, that, in other embodiments, the candidates may be selected differently. In some embodiments, for example in cases where the target structure corresponds to a coronary vasculature, at least three diagnostic images representing different heart phases may be selected. This may also be achieved by analyzing the target structure density measure as a function of the measurement time.

Particularly, in the case of a coronary vasculature, the curve representing the target structure density measure as a function of measurement time may vary over time according to a cyclic variation that is caused by the coronary contraction and expansion. These cyclic variations further allow to determine a (consistent) heart phase for all diagnostic images and, as such, allows a selection of the diagnostic images as candidates based on the determined heart phase. Given that the heart phase may be an important factor for the accuracy of the physiological modeling, the respectively determined heart phase may be considered in the suitability score for each candidate image. It shall be understood, though, that while in some embodiments the heart phase may be derived solely from the cyclic variation of the target structure density measure over time, in other embodiments the deriving may be supported by Electrocardiography (ECG) or by intracoronary pressure data.

In some embodiments, the method may also comprise analyzing the first subset of candidate images, and/or analyzing the third set of candidate images, and determining, for each one of the first subset of candidate images and/or the third subset of candidate images, a visibility measure indicating a visibility of the target structure.

In some embodiments, it may be beneficial to select at least three consecutive images or images obtained in a very short time frame that represent the contrast agent inflow phase or the contrast agent outflow phase as possible candidates, i.e. to further analyze the potential candidate images belonging to the first and the third subsets. Hereby, the analyzing shall be performed to identify three or more candidate images having low foreshortening and low overlap, i.e. that are suitable with respect to visibility of the target structure. Such visibility of the target structure may hereby particularly be expressed in terms of a so-called visibility measure.

Determining such a visibility measure for images from the inflow and/or outflow phase of the contrast agent allows to select candidate images that are particularly suitable for performing a flow velocity assessment through the target structure, thereby allowing to derive important boundary conditions for fluid dynamics modeling such as flow velocity, vessel wall resistance or the like. Similar to the cases above, this may particularly be achieved by analyzing the target structure density measure (indicative of the amount of contrast agent inside the target structure) as a function of measurement time.

In some embodiments, the deriving the plurality of target measures comprises identifying, for each of the plurality of diagnostic images, a motion measure indicative of a motion of the target structure. In some embodiments, the motion measure is identified by determining, for each of the plurality of diagnostic images, the corresponding processed image, and analyzing the processed images as a function of measurement time, wherein the analyzing comprises subtracting two consecutive processed images from one another to determine the motion feature.

In some embodiments, the processed images may also be used to determine the extent of motion of the target structure. This allows to avoid selection of candidate images representing large motion of the target structure and, thus, may even comprise motion blur. For this purpose, the processed images are regarded as a function of the measurement time. This is possible by mapping each processed image to its corresponding diagnostic image that has been obtained at a particular point in measurement time. Thus, the processed images are ordered based on their measurement time, i.e. a series of processed images is obtained. Then, the pixel maps represented in neighboring (consecutive) processed images may be subtracted from one another. Hereby, a large mean absolute difference may indicate that large motion has occurred between the two corresponding diagnostic images. This large mean absolute difference may be used as a motion measure indicative of the motion of said target structure. The larger the value of the motion measure, the more motion is to be expected.

This concept is particularly important in the case of a coronary target structure. The cardiac cycle introduces a coronary motion in the coronary vasculature that may influence the suitability of a particular diagnostic image for physiological modeling. Accordingly, diagnostic images identified as belonging to a particular phase of the cardiac cycle, typically the end diastole, may be preferred over other diagnostic images in terms of motion.

According to some embodiments, the deriving of the plurality of target measures comprises identifying, for each of the plurality of diagnostic images, an overlap measure indicative of an overlap in the target structure.

Another factor that may influence the accuracy of the physiological modeling is the overlap of the target structure. As an example, in case the target structure belongs to a (coronary) vasculature, multiple vessels that are visible in the (two-dimensional) diagnostic images may only be partially be visible due to vessel overlap from the particular direction from which the diagnostic image was taken.

Accordingly, the amount of overlap in a particular diagnostic image may also be considered in the suitability score in terms of a so-called overlap measure. Overlaps may be detected, automatically, by image processing using a target structure specific algorithm and/or manually. In the case of a (coronary) vasculature as the target structure, overlaps may for example be detected by detecting closed loops in the pixel maps represented in the processed images. This is the case since the pixel maps distinguish between background and structure only. A closed loop of higher quantitative values indicating the presence of structure allows to conclude that there are at least two vessels overlapping (since a vessel typically has an inflow and an outflow). In some embodiments, closest loops may particularly be identified by performing contour tracing within the target structure map in the processed image. In some embodiments, orientation scores may be used to determine the closest loops directly from the diagnostic images.

In some embodiments, the deriving of the plurality of target measures comprises receiving additional procedural information, for each of the plurality of diagnostic images. The additional procedural information may comprise information of administered medications that may influence the diagnostic images or the physiological modeling. Examples of such medications are adenosine, nitroglycerin, or acetylcholine. Additional procedural information may further comprise sensor readouts, such as information about pressure, (blood) flow, ECG, or other information that may be acquired along with, at some time before or after acquisition of the diagnostic images. Based on the additional procedural information, further target measures like heart phase, coronary resting state, coronary hyperemic state, or others may be derived.

It shall be understood that the additional procedural information itself may also be regarded as an additional target measure. As an example, diagnostic images that were acquired without administration of nitroglycerin, or too long after said administration may have their suitability score lowered based on this, due to the limited and possibly inconsistent dilation of the coronary arteries. In some embodiments the diagnostic images may only receive a suitability score above 0 if they were acquired directly after an intracoronary adenosine injection since this may be a necessary requirement for the corresponding physiological modeling.

In some embodiments, the deriving of the plurality of target measures comprises identifying, for each of the plurality of diagnostic images, a deviation measure indicative of a deviation from a desired target acquisition time.

In some embodiments, it may be beneficial to select diagnostic images that have been acquired at a particular target acquisition time, in particular when the target structure shows varying motion over time. As an example, if the target structure comprises a coronary vasculature, the cardiac cycle induces cyclic variation in the motion of the vasculature. In this case, a particular target acquisition time may be determined that takes account of this cyclic variation. That is, diagnostic images acquired at this target acquisition time shall be favored over diagnostic images acquired at a different measurement time.

The target acquisition time may thus correspond to an optimum phase in the cardiac cycle. In some specific embodiments, the optimum phase may for example correspond to the end of the diastole. In other embodiments, other phases may be also be used, in particular when previously used diagnostic images have been used in a different phase than the end of the diastole. In this case, the phase to be used for the diagnostic images shall correspond to the phase previously used. That is, the phase consistency over all images should be maintained.

To that end, the diagnostic images not obtained at the target acquisition time need not necessarily be less suitable for physiological modeling. As an example, they may exhibit better contrast or the like which makes them more suitable than the diagnostic image obtained at the target acquisition time. As such, a respective image-specific value for the deviation measure is introduced into the suitability score. The deviation measure is an indicator as to the distance from the selected optimal phase, i.e. the one or more target acquisition times at which the optimum phase is reached. In the case of the coronary physiology, the deviation measure is an indicator of the distance from the optimal stage in the cardiac cycle.

According to some embodiments, the suitability score is based on a weighted sum of the one or more target measures. In some specific embodiments, the suitability score may particularly be based on a weighted sum of the motion measure and/or the overlap measure and/or the deviation measure. In some embodiments, the respective weighting factors are adjusted based on one or more hemodynamic parameters to be modelled using the physiological model to be generated based on one or more images to be selected from the set of candidate images.

In some embodiments, the suitability score indicating as to whether or not a candidate image is particularly suited for generating the physiological model may be derived from a weighted sum of some or all of the above-mentioned measures. In some embodiments, the suitability score may be determined according to $$S_{inflow} = \chi \cdot (1 - w_1 \cdot O - w_2 \cdot M - w_3 \cdot \theta)$$

Hereby, the term $\chi \in (0, 1)$ corresponds to an indicator determined on the basis of the target structure density measure, whereby the indicator indicates if the target structure density measure has identified the corresponding diagnostic image as an image of the first subset representing the contrast agent inflow phase, an image of the second subset representing the contrast agent full filling phase or an image of the third subset representing the contrast agent outflow phase. The term $w_1 \cdot 0$ corresponds to the weighted overlap measure, the term $w_2 \cdot M$ corresponds to the weighted motion measure and the term $w_3 \cdot \theta$ corresponds to the weighted deviation measure.

In some embodiments, the weighting factors $w_1$, $w_2$ and $w_3$ are adjusted depending on the requirements of the physiological model, i.e. the purpose for which the physiological model shall be used. As an example, when selecting an image from the contrast agent inflow phase as a reference for the inflow speed, the weighting factor $w_1$ may be set rather small since the vessel overlap will not be significant at the early contrast agent inflow phase. Accordingly, the overlap measure may be weighted less than the motion measure and/or the deviation measure.

In some embodiments, the (pre-)selected candidate images selected by the method may be presented to a user, in particular a physician, for final selection. In order to ease selection, the candidate images may particularly be presented along with a graphical representation of their suitability score. It shall be understood that the suitability score presented is always specific to the respective physiological model. That is, if the physiological model is used for a different purpose, the suitability score may change.

The suitability score may correspond to a graphical representation of a numerical value shown in or alongside the respective candidate image. In some embodiments, the suitability score may also correspond to a color-coded scale indicating the suitability. Other manners of representing the different suitability scores for each diagnostic image may also be envisioned. By presenting the score in a visual manner, the user may more easily select the images from the candidate images.

In another aspect, an apparatus for selecting one or more diagnostic images for generating a fluid dynamics model, comprising an input unit configured to obtain a plurality of diagnostic images of a target structure, a computation unit configured to derive a plurality of target measures comprising at least one respective target measure for each of the plurality of diagnostic images, an analyzation unit configured to analyze the plurality of target measures, and a selection unit configured to select a set of candidate images based on the analyzing of the plurality of target measures and to assign a suitability score to each candidate image in the set of candidate images, the suitability store indicating a suitability of the respective candidate image for generating the fluid dynamics model. According to yet another embodiment, the selection unit comprises a classifier that has been trained using a training data set correlating one or more diagnostic images with correspondingly measured hemodynamic parameter data.

In some embodiments, an apparatus is provided which is configured to execute the method as described herein above. For that purpose, the apparatus may comprise an input unit, a computation unit, an analyzation unit and a selection unit. Further, in some embodiments, the apparatus may comprise a display unit, such as a liquid crystal display or the like to display a graphical representation of the candidate images and/or their respective suitability score to a user. In some embodiments, the apparatus may further comprise or be communicatively connected to a modeling unit which is used to generate a physiological model from the one or more diagnostic images that have been presented as candidate images particularly suitable for the physiological model and have accordingly be selected by the user. Based on the physiological model one or more hemodynamic parameters, such as pressure, flow velocity, or the like may be simulated, i.e. modeled, for example to perform virtual FFR or iFR.

To that end, the modeling unit may generate the physiological model by segmenting the vessel of interest or vessels of interest represented in the selected diagnostic images and generating a geometric model representing the vessel geometry of the vessel of interest and a fluid dynamics model representing the fluid dynamics through the vessel of interest.

Further, apart from using a programmed algorithm to select the candidate images, it is also possible to provide the apparatus and, in particular, the selection unit with a trained classifier and to use machine learning for image selection. For this purpose, the classifier implementing the machine learning algorithm may be trained from user behavior, i.e. may be trained by tracing the preferred user selection of the candidate images.

Alternatively, or additionally, the classifier may be trained using a training data set. The training dataset may hereby particularly comprise one or more values for measured hemodynamic parameter data, such as pressure values or FFR values or the like, that are correlated with respective diagnostic images. This combination of a diagnostic image and a corresponding hemodynamic parameter value allows to train the best diagnostic image with respect to contrast agent filling, cardiac phase and the like. That is, these factors may be trained by training against measured data.

In some embodiments, the classifier may also be trained to derive the target structure density measure and/or the motion measure and/or the overlap measure and/or the deviation measure based on a training against a measured dataset. In some embodiment, the trained classifier may particularly be trained for overlap detection based on a simulated training dataset to determine the overlap measure.

In a further aspect, a computer program for performing the above-cited method is provided, which, when executed by a processing unit, is adapted to control an apparatus as described above. In an even further aspect, a computer-readable medium is provided having stored thereon the above-cited computer program.

It shall be understood that the method of claim 1, the apparatus of claim 12, the computer program of claim 14 and the computer-readable medium of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
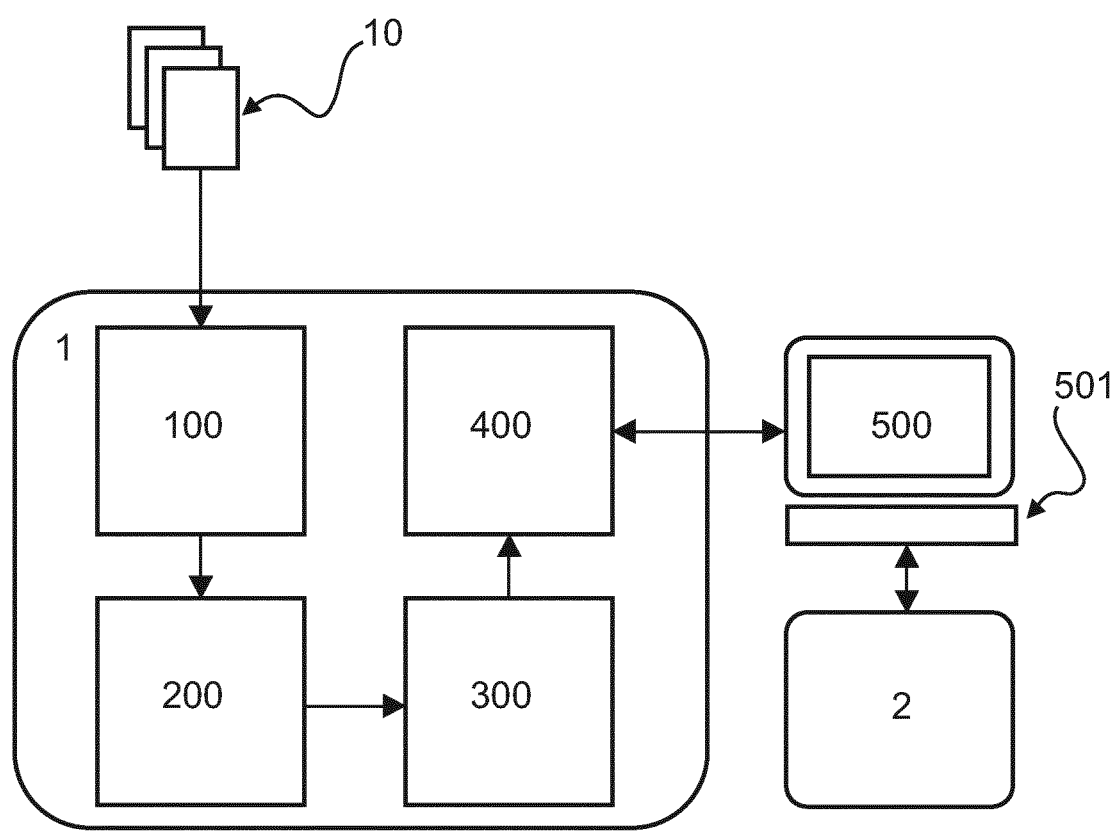
FIG. 1 schematically illustrates an apparatus for image selection according to an exemplary embodiment.

The illustration in the drawings is schematically. In different drawings, similar or identical elements are provided with the same reference numerals.

FIG. 1 represents schematically an exemplary embodiment of an apparatus 1 for performing image selection from a plurality of diagnostic images to obtain one or more candidate images for generating a physiological model. Apparatus 1 comprises an input unit 100, a computation unit 200, an analyzation unit 300 and a selection unit 400. Further, apparatus 1 is communicatively connected to a display unit 500. Display unit 500 is connected to input means 501 and further communicates with modeling unit 2.

In the exemplary embodiment according to FIG. 1, input unit 100 is configured to receive a plurality of diagnostic images 10 and to provide the diagnostic images 10 to computation unit 200. The diagnostic images 10 correspond to X-ray angiography images. It shall be understood, however, that the diagnostic images 10 may also be acquired using a different imaging modality.

Computation unit 200 is then configured to perform image processing on the diagnostic images 10. Hereby, the image processing algorithm used by computation unit 200 is specifically tuned for the target structure which, in the exemplary embodiment according to FIG. 1, corresponds to a coronary vasculature. The processed image comprises a vessel map for the coronary vasculature that highlights the vessel structures. This is achieved by assigning a pixel value indicative of the probability of said pixel belonging to a vessel to each pixel in the diagnostic image. That is, a high pixel value (close to 1) indicates that a pixel most probably belongs to a vessel representation and a low pixel value (close to 0) indicates that a pixel most probably belongs to a background pixel.

In the exemplary embodiment according to FIG. 1, computation unit 200 then analyzes the received processed images by determining a sum of the pixel values per processed image. This sum corresponds to the target structure density measure. Accordingly, a processed image having many pixels with a higher value (i.e. many pixels belonging to a vessel representation) have a higher target structure density measure than the rest. Typically, a higher target structure density measure also corresponds to a higher degree of contrast agent filling since at a lower degree of contrast agent filling many vessel structures would not be visible. Correspondingly, the target structure density measure for images having a lower degree of contrast agent filling of the vessels will be lower.

In the exemplary embodiment according to FIG. 1, computation unit 200 may then provide the target structure density measure, optionally along with the diagnostic images and/or the processed images to analyzation unit 300.

Analyzation unit 300 then analyzes the target structure density measure as a function of measurement time. That is, analyzation unit 300 determines, for each diagnostic image, the point of time at which the particular diagnostic image was obtained and correlates said points in time to the corresponding target structure density measure for the particular diagnostic image. In that context, the term measurement time particularly corresponds to the time from early contrast agent inflow to late contrast agent outflow from the vasculature.

Based on the curve of the target structure density measure, analyzation unit 300 may then distribute the diagnostic images into three subsets of images, namely images belonging to the early contrast agent inflow phase, images belonging to the contrast agent full filling phase and images belonging to the contrast agent outflow phase may be identified.

Figure 2:
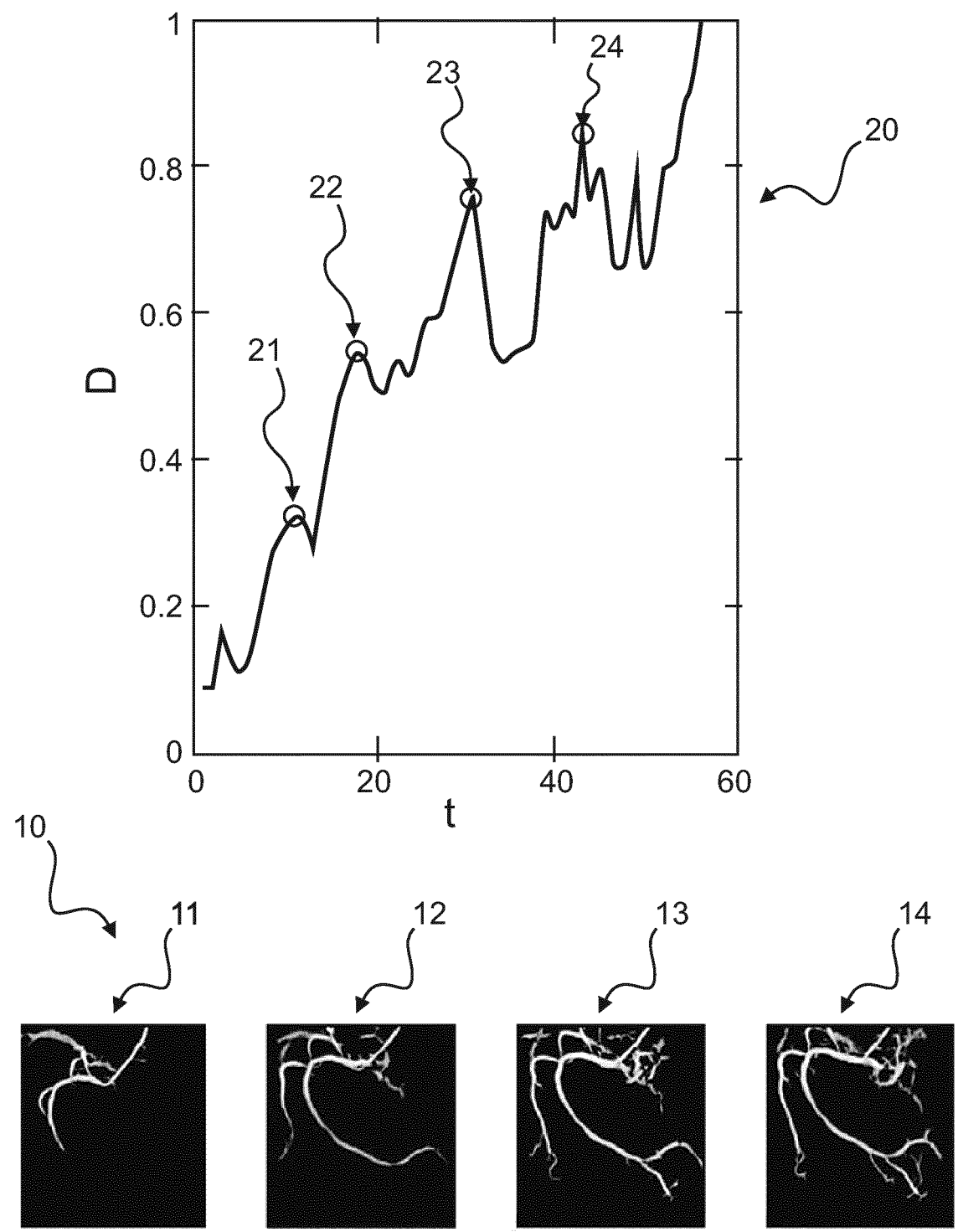
FIG. 2 illustrates an exemplary graphical representation of the analyzing of the target measure as a function of time according to an embodiment.

To that end, FIG. 2 schematically illustrates a graph 20 of the target structure density measure D as function of measurement time t. Below in FIG. 2, a plurality of diagnostic images 10 are shown, the plurality comprising diagnostic images 11, 12, 13 and 14. In the particular embodiment according to FIG. 2, the diagnostic images 11, 12, 13 and 14 correspond to two-dimensional X-ray angiography images. The target structure density measure D corresponds to a density measure indicating the vessel density in each of the diagnostic images.

The target structure density measure D for diagnostic image 11 is indicated as 21 in the graph 20, the target structure density measure D for diagnostic image 12 is indicated as 22, the target structure density measure D for diagnostic image 13 is indicated as 23 and the target structure density measure D for diagnostic image 14 is indicated as 24. Based on these target structure density measures, the diagnostic images 11, 12, 13 and 14 may be assigned to one of the three different phases indicated herein above.

In the exemplary embodiment according to FIG. 2, the target structure density measure 21 for diagnostic image 11 is in the low to intermediate range and increasing. Thus, the diagnostic image 11 belongs to the early contrast agent inflow phase. Similarly, the target structure density measure 22 appears to indicate the contrast agent inflow phase for diagnostic image 12. The target structure density measures 23 and 24 are in the high range. Thus, corresponding diagnostic images 13 and 14 may be considered as belonging to the contrast agent full filling phase.

As may also be appreciated from graph 20, the values for target structure density measure D show a cyclic variation over time. This is due to the cardiac phase. In some embodiments, analyzation unit 300 may use said cyclic variation to derive the heart phase. This allows to determine a consistent heart phase for all candidate images.

Going back to FIG. 1, analyzation unit 300 may thus use the curve representing target structure density measure D as a function of time t to determine, for the diagnostic images 10 whether the respective images belongs to the contrast agent inflow phase, the contrast agent full filling phase or the contrast agent outflow phase. Further, analyzation unit 300 may use the cyclic variation of the curve to determine one consistent heart phase for all diagnostic images.

In the exemplary embodiment according to FIG. 1, analyzation unit 300 may further be configured to determine a motion measure M. For that purpose, analyzation unit 300 may be configured to use the processed images including the vessel mapping by subtracting two neighboring vessel maps, i.e. the vessel maps represented in two processed images derived from two consecutively obtained diagnostic images. By means of subtracting two neighboring images, a mean absolute difference of the neighboring vessel maps may be determined which may be used as a motion measure M. If the value of the mean absolute difference is large, the (coronary) motion is large, whereas if the value is small, the motion may also be assumed to be small. That is, a higher value for motion measure M indicates more motion than a smaller value.

Analyzation unit 300 may further be configured to determine an overlap measure O. In the exemplary embodiment according to FIG. 1, analyzation unit 300 may be configured to identify, in each map as represented in the processed images, closed loops. These closed loops may be considered to indicate overlapping vessels. Based on these closed loops, analyzation unit 300 may then determine, for each processed image, an overlap measure O indicating the amount of overlap in the corresponding diagnostic image 10.

In the exemplary embodiment according to FIG. 1, analyzation unit 300 may then provide the plurality of diagnostic images, their corresponding target structure density measures and motion as well as overlap measures and, optionally, the plurality of processed images to selection unit 400. Selection unit 400 may receive the plurality of diagnostic images, the target measures, the motion measures and the overlap measures as well as the plurality of processed images (if provided) and may use these information to determine, for each diagnostic image of the plurality of diagnostic images, a respective suitability score, indicating the diagnostic image's suitability for a particular purpose. In the embodiment according to FIG. 1, those diagnostic images shall be selected by selection unit 400 which are most suitable for generating a physiological model including a geometric model and a fluid dynamics model of the coronary vasculature for the purpose of deriving one or more hemodynamic parameters for said coronary vasculature as target structure.

In the exemplary embodiment according to FIG. 1, selection unit 400 calculates the suitability score S according to $$S = \chi \cdot (1 - w_1 \cdot O - w_2 \cdot M - w_3 \cdot \theta)$$

whereby the term $\chi \in (0, 1)$ corresponds to an indicator determined on the basis of the target structure density measure, said indicator indicating if the target structure density measure has identified the corresponding diagnostic image as an image of the first subset representing the contrast agent inflow phase, an image of the second subset representing the contrast agent full filling phase or an image of the third subset representing the contrast agent outflow phase. The term $w_1 \cdot O$ corresponds to a product of the overlaying feature with a corresponding weighting factor. Further, the term $w_2 \cdot M$ corresponds to the product of the motion measure with a corresponding weighted factor.

In the exemplary embodiment according to FIG. 1, in which the target structure is a coronary vasculature, the term $w_3 \cdot \theta$ is further considered. The $\theta$ corresponds to a deviation measure indicating the distance of the particular image from the optimal phase in the cardiac cycle. In the embodiment of FIG. 1, this optimal phase corresponds to the end diastole. Accordingly, the deviation measure $\theta$ indicates the distance from said end of diastole. The factor $w_3$ corresponds to a weighting factor for said deviation measure.

In the embodiment according to FIG. 1, the weighting factors $w_1$, $w_2$ and $w_3$ are adjusted depending on the requirements for the image-based physiological model. As an example, a reference for the inflow speed is needed for the fluid dynamics model. In this case, the weighting factor $w_1$ for the overlap measure may be set rather small. This is the case since, in the early contrast agent inflow phase, only little contrast agent is inside the vessels and, thus, the overlap of the vessels may be negligible. In contrast, when selecting an image from the contrast agent full filling phase, the overlap measure shall be weighted higher, since, at this stage, the vessel overlap is more significant.

The suitability score S may thus be determined as the product of the indicator for the target structure density measure times a factor determined as 1 minus a weighted sum of the motion measure, the overlap measure and the deviation measure. The resulting score is thus higher the smaller the influence of said features. A high suitability score therefore indicates a high chance that the diagnostic image may render promising results.

In the embodiment according to FIG. 1, computation unit 400 determines the suitability scores S to derive a set of candidate images and provides these candidate images along with their respective suitability scores to display unit 500. Display unit 500 generates a graphical representation of each of the received candidate images and displays said graphical representation to the user. Optionally, the suitability score may be displayed alongside the respective candidate image.

The user may thus browse through a set of candidate images automatically pre-selected based on their suitability for the physiological modeling. This allows the user to review these candidate pictures only, as they are objectively the best images available.

The user may then, via user interface 501, select one or more diagnostic images (based on a visual inspection and/or the suitability score) and prompt the display device to provide the (finally) selected diagnostic images to modeling unit 2. Modeling unit 2 then uses the one or more selected images to generate a physiological model including a geometric model and a fluid dynamics model. The generated model may then be provided to the display device 500 again and a graphical representation thereof may be presented to the user.

FIG. 2 represents schematically a flow chart for a method for image selection according to an embodiment. In step S101, a plurality of diagnostic images 10 are received at input unit 100. In step S102, input unit 100 provides these diagnostic images 10 to computation unit 200.

In step S201, the diagnostic images 10 are received at computation unit 200. In step S202, computation unit 200 processes the diagnostic images using an image processing algorithm that is specifically tuned for the target structure which, in the exemplary embodiment presented herein, corresponds to a coronary vasculature. By means of the processing, a processed image is obtained for each diagnostic image that comprises a vessel map for the coronary vasculature. This is achieved by assigning a pixel value indicative of the probability of said pixel belonging to a vessel to each pixel in the diagnostic image. In step S203, a sum of the pixel values of the pixels in each processed image is calculated to determine the target structure density measure. In step S204, the target structure density measure for each image, the plurality of processed images derived from the plurality of diagnostic images and the plurality of diagnostic images are provided to the analyzation unit 300.

In step S301, analyzation unit receives the plurality of processed images, the plurality of diagnostic images and the target structure density measure. In step S302, analyzation unit 300 plots the target structure density measure as a function of measurement time for further analysis. In step S303, analyzation unit 300 analyzes the curve of the target structure density measure as a function of time and identifies, based on said analysis, whether a respective image belongs to the early contrast agent inflow phase, to the contrast agent full filling phase or to the contrast agent outflow phase as described in relation to FIG. 2. In step S304, analyzation unit 300 further uses the curve of the target structure density measure to determine the heart phase at which each diagnostic image was obtained. This allows to provide a consistent heart phase for all candidate images that may be suggested to the user.

Figure 3:
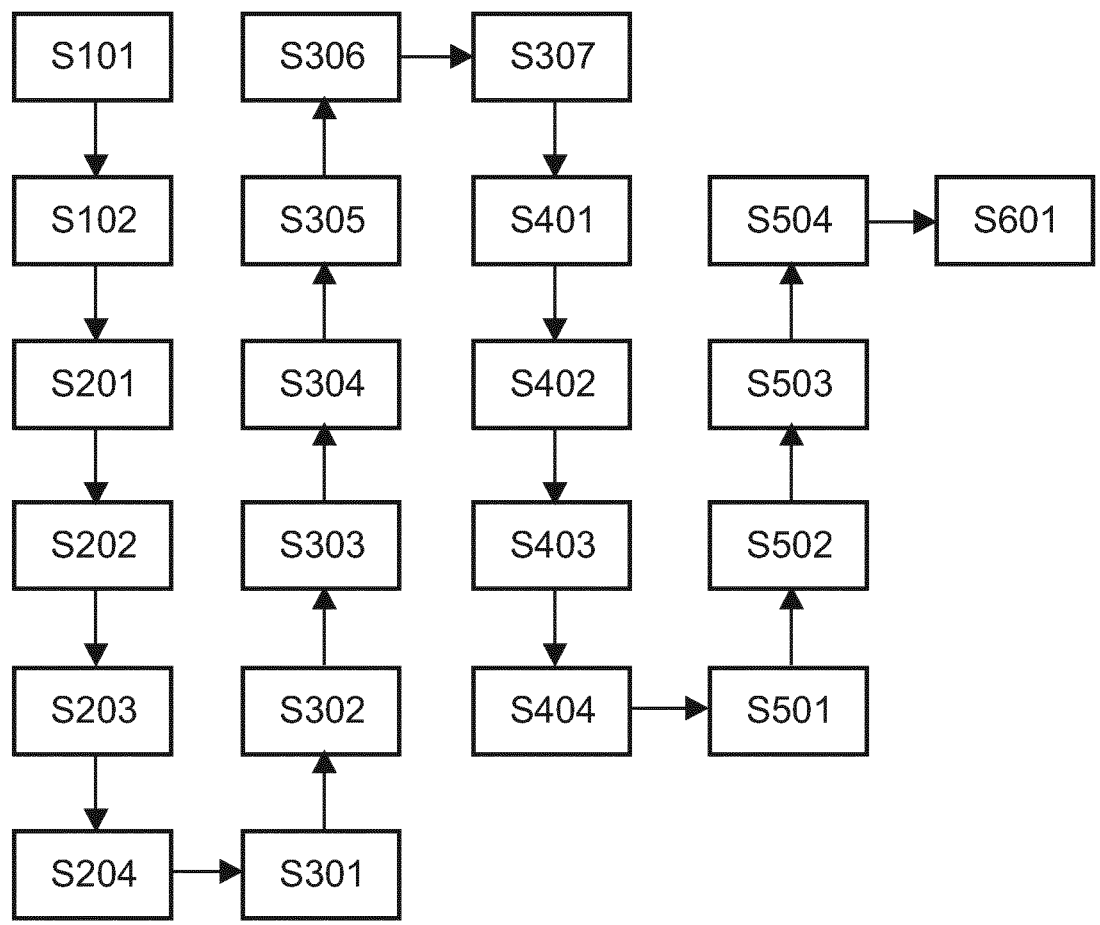
FIG. 3 illustrates an exemplary selection method according to an embodiment.

In step S305, analyzation unit 300 determines a motion measure M. In the exemplary embodiment according to FIG. 3, this is achieved by subtracting the vessel mapping of two neighboring processed images to obtain a mean absolute difference of the neighboring vessel maps. The mean absolute difference may then be used as motion measure M, whereby a larger value indicates large coronary motion and a smaller value indicates smaller coronary motion. It shall be understood that the output of step S305 shall comprise a motion measure value for each diagnostic image that has been considered.

In step S306, analyzation unit 300 further determine an overlap measure O by identifying closed loops appearing in the respective vessel maps as shown in each of the plurality of processed images. Depending on how many closed loops are identified per processed image, the overlap measure O is set to indicate the amount of overlap in one particular diagnostic image which corresponds to the respective processed image. It shall be understood that the output of step S306 typically comprises an overlap measure value for each diagnostic image that has been considered.

In step S307, analyzation unit 300 provides the plurality of diagnostic images, their target structure density measures as well as their determined motion and overlap measure and, optionally, the processed image to selection unit 400.

In step S401, selection unit 400 receives the plurality of diagnostic images, their respective target structure density measures, motion and overlap measures and the plurality of processed images (if provided).

In step S402, selection unit 400 considers the requirements of the process the images are needed for. In the particular embodiment of FIG. 2, the diagnostic images shall be used for generating a physiological model including a geometric model and a fluid dynamics model. Based on these requirements, selection unit 400 sets respective weighting factors for each of the motion measure and the overlap measure. Further, selection unit derives, for each diagnostic image, a deviation measure indicating the distance from the optimal phase in the cardiac cycle and a corresponding weighting factor that also depends on the requirements set out by the modeling process to the diagnostic images.

In step S403, selection unit 400 determines the suitability scores S as described herein above in relation to FIG. 1 in order to (pre-)select a set of candidate images. In step S404, selection unit 400 provides these candidate images along with their respective suitability scores to display unit 500.

In step S501, display unit 500 receives the set of candidate images that have been pre-selected and their respective suitability scores and, in step S502, generates a graphical representation of each candidate image in the set of candidate images. In step S503, display unit 500 displays the graphical representation of each one from the set of candidate images, which may optionally include the corresponding suitability score, to the user.

In step S504, the user reviews the presented set of candidate images and selects one or more diagnostic as represented in the set of candidate images. This selection prompts the selected one or more diagnostic images to be provided to modeling unit 2 in step S601. In response to the receiving of the one or more selected diagnostic images, modeling unit 2 generates a physiological model including a geometric model and a fluid dynamics model for hemodynamic simulation. Thus, a method is enabled which allows to select diagnostic images in an efficient and quick manner without many user interactions necessary.

Although in the above-cited embodiments, the diagnostic images have been acquired using X-ray angiography, it shall be understood that other imaging modalities may likewise be used, such as computed tomography, ultra sound imaging, magnetic resonance imaging or the like.

Further, while in the above embodiments, the method was applied to a coronary vasculature, it shall be understood that the method may equally be used for image selection of images of different target structures, in particular, target structure representing different parts of the human and/or animal body.

Also, while in the above-described embodiments, the selection has been based on the target structure density measure and a (weighted) motion measure, overlap feature and deviation measure, it shall be understood that further factors may be included into the selection, such as C-arm angulation, aortic pressure values, absence of intravascular devices such as IVUS or guide wires, and/or the frame rate.

Further, while in the above-cited embodiments, the selection has been performed by a handcrafted algorithm, it shall be understood that machine learning based methods may also be used for image selection- Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the generating of the processed images, the deriving of the plurality of target measures, the analyzing of the plurality of target measures, the selecting of the candidate images and/or the determining and the assigning of the suitability score et cetera performed by one or several units or devices can be performed by any other number of units or devices. These procedures in accordance with the invention can hereby be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a method of selecting one or more diagnostic images for generating a fluid dynamics model, the method comprising the steps of obtaining a plurality of diagnostic images of a target structure, deriving a plurality of target measures comprising at least one respective target measure for each of the plurality of diagnostic images, analyzing the plurality of target measures to select a set of candidate images, and assigning a suitability score to each candidate image in the set of candidate images, the suitability store indicating a suitability of the respective candidate image for generating the fluid dynamics model.

By means of the method and apparatus for image selection, an automatic image selection process may be established with allows to pre-select a set of candidate images such that the user may find the most suitable diagnostic images more quickly and with a reduced amount of user interaction.

The invention claimed is:

1. A computer-implemented method of selecting one or more diagnostic images for generating a physiological model of a target structure, the method comprising:
   obtaining a plurality of diagnostic images of the target structure,
   deriving a plurality of target measures indicating one or more properties of the target structure in the plurality of diagnostic images, wherein at least one target measure is derived for each of the plurality of diagnostic images,
   analyzing the plurality of target measures to select, from the plurality of diagnostic images, a set of candidate images, and
   assigning a suitability score to each candidate image in the set of candidate images, the suitability score indicating a suitability of the respective candidate image for generating the physiological model of the target structure, wherein the suitability score is assigned based on the one or more properties of the target structure indicated in the respective candidate image being suitable to model a physiological aspect of the target structure.

2. The method according to claim 1, wherein the deriving of the plurality of target measures comprises:
   generating, for each of the plurality of diagnostic images, a respective processed image, the generating comprising assigning a plurality of quantitative values to a plurality of pixels of the respective processed image, a quantitative value indicating a probability that a pixel represents the target structure, and
   deriving a target structure density measure for each of the plurality of diagnostic images based on the plurality of quantitative values.

3. The method according to claim 2, wherein the target structure density measure for each of the plurality of images is derived based on a sum of the plurality of quantitative values.

4. The method according to claim 2, wherein the selecting the set of candidate images comprises:
   analyzing the derived target structure density measure as a function of measurement time, and
   obtaining, based on the analyzing of the derived target structure density measure:
      a first subset of candidate images representing a contrast agent inflow phase;
      a second subset of candidate images representing a contrast agent full filling phase; and
      a third subset of candidate images representing a contrast agent outflow phase.

5. The method according to claim 4, further comprising:
   analyzing at least one of the first subset of candidate images or the third subset of candidate images, and
   determining, for each one of the at least one of the first subset of candidate images or the third subset of candidate images, a visibility measure indicating a visibility of the target structure.

6. The method according to claim 2, wherein the deriving of the plurality of target measures comprises:
   identifying, for each of the plurality of diagnostic images, a motion measure indicative of a motion of the target structure.

7. The method according to claim 6, wherein the motion measure is identified by:
   determining, for each of the plurality of diagnostic images, the respective processed image, and
   analyzing the respective processed image as a function of measurement time, wherein the analyzing of the respective processed image comprises subtracting two consecutive processed images from one another to determine the motion measure.

8. The method according to claim 1, wherein the deriving of the plurality of target measures comprises:
   identifying, for each of the plurality of diagnostic images, an overlap measure indicative of an overlap in the target structure.

9. The method according to claim 1, wherein the deriving of the plurality of target measures comprises:
   identifying, for each of the plurality of diagnostic images, a deviation measure indicative of a deviation from a desired target acquisition time.

10. The method according to claim 1, wherein the suitability score is based on a weighted sum of the plurality of derived target measures.

11. The method according to claim 10, whereby respective weighting factors are adjusted based on one or more hemodynamic parameters to be modelled using the physiological model to be generated based on one or more images to be selected from the set of candidate images.

12. An apparatus for selecting one or more diagnostic images for generating a physiological model of a target structure, the apparatus comprising:
   a processor in communication with memory, the processor configured to:
      obtain a plurality of diagnostic images of the target structure,
      derive a plurality of target measures indicating one or more properties of the target structure in the plurality of diagnostic images, wherein at least one respective target measure is derived for each of the plurality of diagnostic images,
      analyze the plurality of target measures to select a set of candidate images, and
      assign a suitability score to each candidate image in the set of candidate images, the suitability store indicating a suitability of the respective candidate image for generating the physiological model of the target structure, wherein the suitability score is assigned based on the one or more properties of the target structure indicated in the respective candidate image being suitable to model a physiological aspect of the target structure.

13. The apparatus according to claim 12, wherein the processor is further configured to:
   apply a model that has been trained using a training data set correlating one or more diagnostic images with correspondingly measured hemodynamic parameter data.

14. A non-transitory computer-readable storage medium having stored a computer program comprising instructions, which, when executed by a processor, cause the processor to:
   obtain a plurality of diagnostic images of a target structure,
   derive a plurality of target measures indicating one or more properties of the target structure in the plurality of diagnostic images, wherein at least one respective target measure is derived for each of the plurality of diagnostic images,
   analyze the plurality of target measures to select a set of candidate images, and assign a suitability score to each candidate image in the set of candidate images, the suitability score indicating a suitability of the respective candidate image for generating a physiological model of the target structure, wherein the suitability score is assigned based on the one or more properties of the target structure indicated in the respective candidate image being suitable to model a physiological aspect of the target structure.

15. The apparatus according to claim 12, wherein the processor is further configured to:

generate, for each of the plurality of diagnostic images, a respective processed image, the generating comprising assigning a plurality of quantitative values to a plurality of pixels of the respective processed image, a quantitative value indicating a probability that a pixel represents the target structure, and derive a target structure density measure for each of the plurality of diagnostic images based on the plurality of quantitative values.

16. The apparatus according to claim 15, wherein the processor is further configured to:

derive the target structure density measure for each of the plurality of diagnostic images based on a sum of the plurality of quantitative values.

17. The apparatus according to claim 15, wherein the processor is further configured to:

analyze the derived target structure density measure as a function of measurement time, and obtain, based on the analysis of the derived target structure density measure:
 a first subset of candidate images representing a contrast agent inflow phase;
 a second subset of candidate images representing a contrast agent full filling phase; and
 a third subset of candidate images representing a contrast agent outflow phase.

18. The non-transitory computer-readable storage medium of claim 14, wherein the instruction, when executed by the processor, further cause the processor to:

generate, for each of the plurality of diagnostic images, a respective processed image, the generating comprising assigning a plurality of quantitative values to a plurality of pixels of the respective processed image, a quantitative value indicating a probability that a pixel represents the target structure, and derive a target structure density measure for each of the plurality of diagnostic images based on the plurality of quantitative values.

19. The non-transitory computer-readable storage medium of claim 18, wherein the instruction, when executed by the processor, further cause the processor to:

derive the target structure density measure for each of the plurality of diagnostic images based on a sum of the plurality of quantitative values.

20. The non-transitory computer-readable storage medium of claim 18, wherein the instruction, when executed by the processor, further cause the processor to:

analyze the derived target structure density measure as a function of measurement time, and obtain, based on the analysis of the derived target structure density measure:
 a first subset of candidate images representing a contrast agent inflow phase;
 a second subset of candidate images representing a contrast agent full filling phase; and
 a third subset of candidate images representing a contrast agent outflow phase.

\* \* \* \* \*